United States Patent [19]

Oshiro et al.

[11] Patent Number: 5,006,528
[45] Date of Patent: Apr. 9, 1991

[54] CARBOSTYRIL DERIVATIVES

[75] Inventors: Yasuo Oshiro, Tokushima; Seiji Sato, Itano; Nobuyuki Kurahashi, Tokushima, all of Japan

[73] Assignee: Otsuka Pharmaceutical Co., Ltd., Tokyo, Japan

[21] Appl. No.: 424,719

[22] Filed: Oct. 20, 1989

[30] Foreign Application Priority Data

Oct. 31, 1988 [JP] Japan .................................. 63-276953

[51] Int. Cl.$^5$ ..................... A61K 31/00; C07D 401/12
[52] U.S. Cl. ...................................... 514/253; 544/363
[58] Field of Search .......................... 544/363; 514/253

[56] References Cited

U.S. PATENT DOCUMENTS 4,824,840 4/1989 Banno et al. ........................ 544/363

FOREIGN PATENT DOCUMENTS 58-203968 11/1983 Japan .................................. 544/363

*Primary Examiner*—Frederick E. Waddell
*Assistant Examiner*—James H. Turnipseed
*Attorney, Agent, or Firm*—Finnegan, Henderson, Farabow, Garrett & Dunner

[57] ABSTRACT

A novel carbostyril derivative and salt thereof represented by the formula (1)

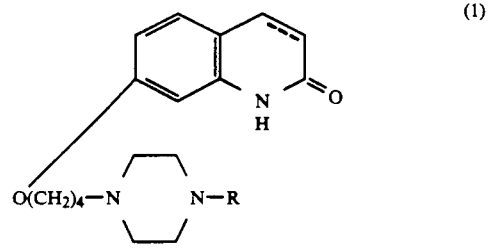

(wherein R is a group of the formula

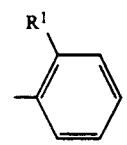

((wherein $R^1$ is a $C_1$-$C_3$ alkoxy group)), a group of the formula

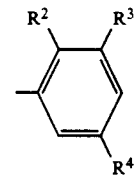

((wherein $R^2$ and $R^3$ are each, at the same time, a chlorine atom, a bromine atom; and $R^4$ is a hydrogen atom or a chlorine atom)), 2-methyl-3-nitrophenyl group, 3,5-dichlorophenyl group, or a group of the formula

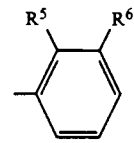

((wherein $R^5$ is a chlorine atom or a bromine atom; and $R^6$ is a methyl group)); the carbon-carbon bond between 3- and 4-position in the carbostyril skeleton is a single or double bond).

21 Claims, No Drawings

CARBOSTYRIL DERIVATIVES

FIELD OF THE INVENTION

The present invention relates to novel carbostyril derivatives. More particularly, the invention relates to novel carbostyril derivatives and salts thereof, processes for preparing said carbostyril derivatives and salts thereof, as well as pharmaceutical compositions for treating schizophrenia containing, as the active ingredient, said carbostyril derivative or salt thereof.

BACKGROUND OF THE INVENTION

Schizophrenia is the most common type of psychosis caused by an excessive neurotransmission activity of the dopaminergic nervous system in the central nervous system. [Cf. "Hypothesis of Excessive Dopamine" by Michio Tohru: TAISHA (Metabol:sm), Vol. 22, pp. 49, (1985); and Pharmacia Review, No. 10, "KOKORO-TO-KUSURI (Mind and Drugs)" edited by Pharmaceutical Society of Japan.]

Heretofore, a number of drugs, having the activity for blocking the neurotransmission of dopaminergic receptor in the central nervous system, have been developed, the example for said drugs are phenothiazine-type compounds such as Chlorpromazine; butyrophenone-type compounds such as Haloperidol; and benzamide-type compounds such as Sulpiride. These known drugs are now used widely for the purpose of improving so-called positive symptoms in the acute period of schizophrenia such as hallucinations, delusions and excitations and the like.

However, many of these drugs are considered as not effective for improving so-called the negative symptoms which are observed in the chronic period of schizophrenia such as apathy, emotional depression, hypopsychosis and the like. In addition to the above, these drugs give important side-effects such as akathisia, dystonia, Parkinsonism dyskinesia and late dyskinesia and the like, which are caused by blocking the neurotransmission of dopaminergic receptor in the striate body. Furthermore, other side-effects such as hyperprolactinemia and the like given by these drugs are become other problems. [Cf. G. M. Simpson, E. H. Pi, and J. J. Sramek, Jr.: Drugs, Vol. 21, pp. 138 (1981).]

Under these circumstances, development of drugs for treating schizophrenia having safety and clinically effectiveness have been eagerly expected.

The present inventors have made an extensive study for the purpose of developing drugs for treating schizophrenia, which would be not only effective for improving the negative symptoms, but also effective for improving the positive symptoms of schizophrenia, furthermore such drugs would have less side-effects as compared with those shown by drugs known in prior art. As the result, the present inventors have successfully found carbostyril derivatives having strong activity for blocking neurotransmission of dopaminergic receptor. As to the side-effects given by known drugs for treating schizophrenia are for example, in the case of phenothiazine-type drugs, the orthostatic hypotension and hypersedation on the basis of strong α-blocking activity; and in the case of drugs having strong activity for blocking neurotransmission of dopaminergic receptor, the side-effects are so-called extrapyramidal tract syndromes such as catalepsy, akathisia, dystonia and the like caused by the blocking neurotransmission of dopaminergic receptor in the atriate body.

Among carbostyril derivatives known in prior art, those disclosed in U.S. Pat. No. 4,734,416; Canadian Patent No. 1,117,110; British Patent No. 2,017,701; German Patent Nos. 2,911,108, 1,912,105 and 2,953,723; Japanese Patent Kokai (Laid-open) Nos. 54-130,587 (1979), 55-127,371, (1980) and 62-149,664 (1987) are having chemical structural formulas of upper conception of carbostyril derivatives of the present invention.

Furthermore, carbostyril derivatives disclosed in U.S. Pat. No. 4,234,585 and European Patent No. 226,441 have chemical structural formula similar to that of carbostyril derivatives of the present invention, but the pharmacological activities thereof are different from those of possessed by the carbostyril derivatives of the present invention.

In addition to the above, the carbostyril derivatives disclosed in U.S. Pat. No. 4,234,584 have chemical structural formula similar to that of carbostyril derivatives of the present invention and also have pharmacological activities similar to those of shown by carbostyril derivatives of the present invention.

Carbostyril derivatives disclosed in Australian Patent No. 50252/85, Japanese Patent Kokai (Laid-open) Nos. 58-43952 (1983), 56-49359 (1981), 56-49360 (1981) and 56-49361 (1981) have substituents different from those of the carbostyril derivatives of the present invention.

SUMMARY OF THE INVENTION

It is an object of the present invention to provide novel carbostyril derivatives and salts thereof.

A further object of the present invention is to provide processes for preparing said carbostyril derivatives and salts thereof.

A still further object of the present invention is to provide a pharmaceutical composition for treating schizophrenia.

DETAILED DESCRIPTION OF THE PREFERRED EMBODIMENTS

Carbostyril derivatives of the present invention and salts thereof are represented by the general formula (1) as follows:

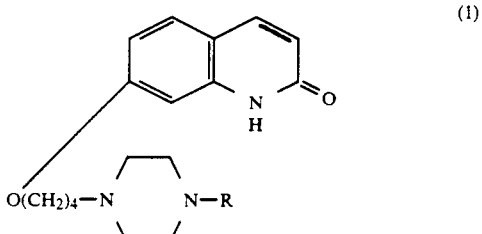

(1)

(wherein R is a group of the formula

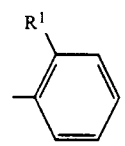

(wherein $R^1$ is a $C_1$–$C_3$ alkoxy group)), a group of the formula

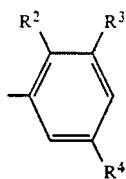

wherein $R^2$ and $R^3$ are each, at the same time, a chlorine atom, a bromine atom; and $R^4$ is a hydrogen atom or a chlorine atom, 2-methyl-3-nitrophenyl group, 3,5-dichlorophenyl group, or a group of the formula

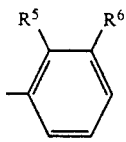

wherein $R^5$ is a chlorine atom or a bromine atom; and $R^6$ is a methyl group; the carbon-carbon bond between 3- and 4-positions in the carbostyril skeleton is a single or double bond), and salts thereof.

Carbostyril derivatives and salts thereof represented by the general formula (1) possess strong activity for blocking the neurotransmission effect of dopaminergic receptor, with a weak α-blocking activity which have been found during the step of research and development of a number of carbostyril derivatives, thus when the strength of α-blocking activity of a carbostyril derivative is defined as the dose ($ED_{50}$, mg/kg, per os) which is required to inhibits 50% of deth of mice being administered with epinephrine, and also the strength of activity for blocking the neurothransmission effect of dopaminergic receptor which is the main activity of carbostyril derivative, is defined as the dose ($ED_{50}$, mg/kg, per os) which is required to inhibits 50% of stereotypy of mice induced by administration with apomorphine, the agonist of dopamine. The present invention was successfully completed by the above-mentioned findings of said activitied.

Carbostyril derivatives represented by the general formula (1) can be prepared by various methods, the examples for said methods are as follows:

Reaction Formula-1

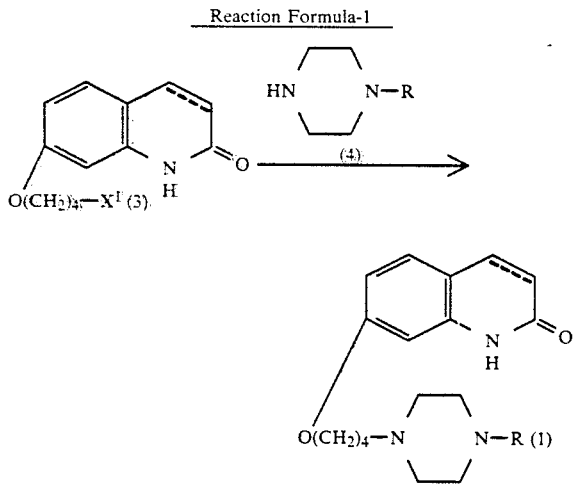

(wherein R and the carbon-carbon bond between 3- and 4-positions in the carbostyril skeleton are the same as defined above; and $X^1$ is a halogen atom or a group which can carry out a substitution reaction similar to a halogen atom, the examples of such group is a mesityloxy group and tosyloxy group and the like).

The reaction of a compound of the general formula (3) with a compound of the general formula (4) can be carried out in the absence or presence of a common inert solvent, under temperature condition of room temperature to 200° C., preferably at 60° to 120° C., and the reaction is completed in about several hours to 24 hours. As to the inert solvent used in this reaction, any solvents for example, ethers such as dioxane, tetrahydrofuran, ethylene glycol dimethyl ether and the like; aromatic hydrocarbons such as benzene, toluene, xylene and the like; lower alcohols such as methanol, ethanol, isopropanol and the like; polar solvents such as dimethylformamide (DMF), dimethyl sulfoxide (DMSO), acetonitrile and the like can be used. The reaction can be advantageously carried out by using a basic compound as the dehydrohalogenating agent. As to said basic compound, an inorganic basic compound such as calcium carbonate, sodium carbonate, sodium hydroxide, sodium hydrogen carbonate, sodium amide, sodium hydride and the like; and an organic basic compound such as triethylamine, tripropylamine, pyridine, quinoline and the like can be used. Furthermore, the above-mentioned reaction can be carried out, if necessary, by adding an alkali metal iodide such as potassium iodide, sodium iodide or the like as the reaction accelarator. In the above-mentioned reaction, the ratio of used amount of a compound of the general formula (3) to a compound of the general formula (4) may be an equimolar quantity or more, preferably an equimolar quantity to 5 times the molar quantity, more preferably, an equimolar quantity to 1.2 times the molar quantity of the latter to the former.

Reaction Formula-2

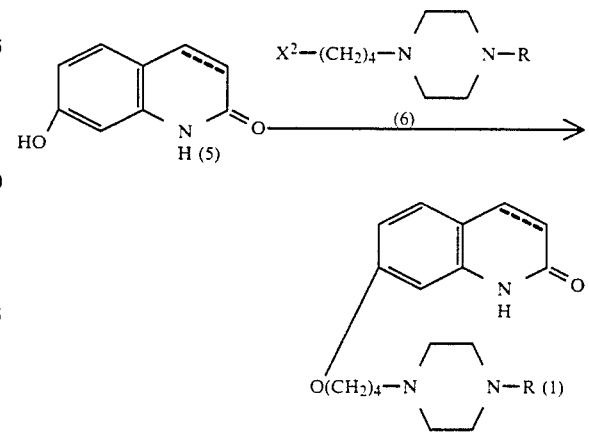

(wherein R and the carbon-carbon bond between 3- and 4-positions in the carbostyril skeleton are the same as defined above; and $X^2$ is a halogen atom).

In the Reaction Formula-2, the reaction of a compound represented by the general formula (5) with a compound represented by the general formula (6) can be carried out, preferably by using a basic compound as the dehydrohalogenating agent, in a suitable solvent at room temperature to 200° C., preferably at 50° to 150° C. for within several hours to 15 hours. As to the suitable solvent used in the above reaction, lower alcohols such as methanol, ethanol, isopropanol and the like; ketones such as acetone, methyl ethyl ketone and the like; ethers such as dioxane, diethylene glycol dimethyl ether and the like; aromatic hydrocarbons such as toluene, xylene and the like; DMF, DMSO, hexamethylphosphoryl triamide and the like can be exemplified. As to the basic compound to be used as the dehydrohalogenating agent, an inorganic basic substance such as sodium hydorxide, potassium hydroxide, sodium carbonate, potassium carbonate, sodium hydride, metallic potassium, sodium amide and the like; an alkali metal alcoholate such as sodium methoxide, sodium ethoxide, potassium ethoxide and the like; as well as an organic basic compound for example, tertiary amines such as pyridine, quinoline, triethylamine, tripropylamine and the like can be exemplified. Furthermore, the above-mentioned reaction can be carried out by using an alkali metal iodide such as potassium iodide, sodium iodide and the like as the reaction accelerator. The ratio of used amount of a compound of the formula (5) to compound of the formula (6) is not specifically restricted, and an equimolar quantity or more of the latter, generally an equimolar to 5 times the molar quantity, preferably an equimolar to 1.2 times of the molar quantity of the latter may be used to one molar quantity of the former.

Reaction Formula-3

Reaction Formula-3

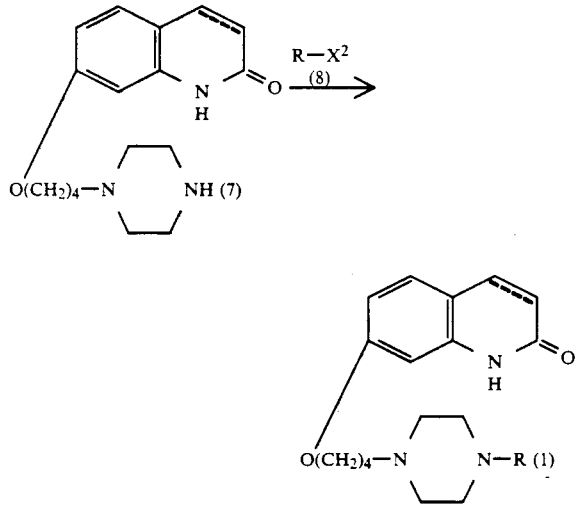

(wherein R, $X^2$ and the carbon-carbon bond between 3- and 4-positions in the carbostyril skeleton are the same as defined above).

The reaction of a compound of the general formula (7) with a compound of the general formula (8) is carried out in a suitable solvent, and in the absence or presence of a basic compound. As to the solvent used in this reaction, aromatic hydrocarbons such as benzene, toluene, xylene and the like; lower alcohols such as methanol, ethanol, propanol, butanol and the like; pyridine, acetone, DMF, DMSO, hexamethylphosphoryl triamide and the like can be exemplified. As to the basic compound used in this reaction, inorganic basic compounds such as sodium carbonate, potassium carbonate, sodium hydrogen carbonate, potassium hydrogen carbonate, sodium hydroxide, potassium hydroxide, sodium hydride, potassium hydride and the like; organic basic compounds such as triethylamine and the like can be exemplified. A compound of the general formula (8) may be used at least an equimolar quantity, preferably an equimolar to 3 times the molar quantity thereof to one molar quantity of a compound of the general formula (7). The reaction is carries out, generally at room temperature to 180° C., preferably at 80° to 150° C., and is completed in about 3 to 30 hours.

Reaction Formula-4

Reaction Formula-4

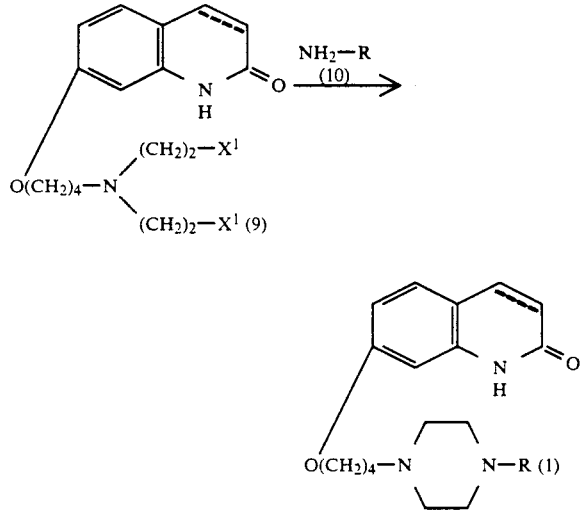

(wherein R, $X^1$ and the carbon-carbon bond between 3- and 4- positions in the carbostyril skeleton are the same as defined above).

The reaction of a compound of the formula (9) with a compound of the formula (10) can be carried out in a suitable solvent and in the absence or presence of a basic compound. As to the solvent used in this reaction, water; a lower alcohols such as methanol, ethanol, isopropanol, butanol and the like; aromatic hydrocarbons such as benzene, toluene, xylene and the like; acetic acid, ethyl acetate, DMF, DMSO, hexamethylphosphoryl triamide and the like can be exemplified. As to the basic compound used in this reaction, an inorganic basic compound such as sodium carbonate, potassium carbonate, sodium hydrogen carbonate, sodium hydroxide, potassium hydroxide and the like; an alkali metal alcoholate such as sodium methylate, sodium ethylate and the like; an organic basic compound such as 1,5-diazabicyclo[4.3.0]nonene-5 (DBN), 1,8-diazabicyclo[5.4.0]-undecene-7 (DBU), 1,4-diazabicyclo[2.2.2]octane (DABCO) and the like can be exemplified. A compound of the general formula (10) may be used generally, at least an equimolar quantity, preferably an equimolar to 5 times the molar quantity to one molar quantity of compound of the general formula (9). The reaction is generally carried out at 40° to 120° C., preferably at about 70° to 100° C., and is completed in about 1 to 15 hours.

Reaction Formula-5

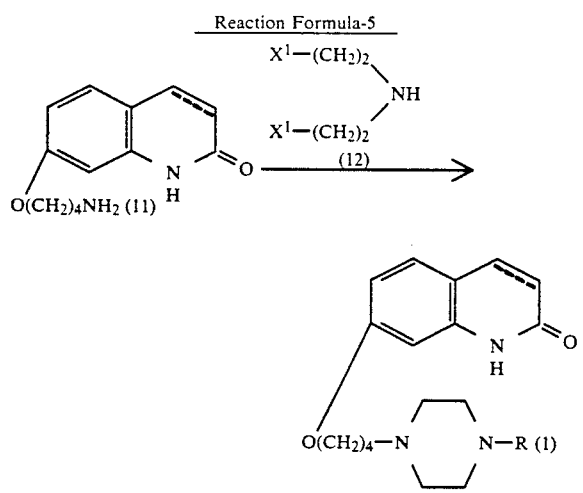

(wherein R, $X^1$ and the carbon-carbon bond between 3- and 4-positions in the carbostyril skeleton are the same as defined above).

The reaction of a compound of the general formula (11) with a compound of the general formula (12) is carried out under conditions similar to those employed in the reaction of a compound of the general formula (9) with a compound of the general formula (10).

In the above-mentioned Reaction Formula-1, a compound of the general formula (4) used as one of the starting materials is prepared by a method as shown in Reaction Formula-6 as follows.

Reaction Formula-6

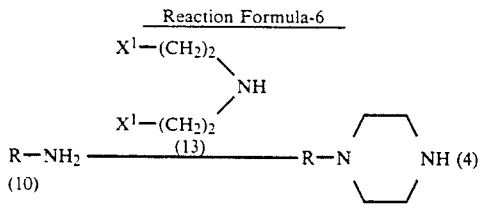

(wherein R and $X^1$ are the same as defined above).

The reaction of a compound of the formula (10) with a compound of the formula (13) is carried out by methods similar to those employed in the reaction of a compound of the formula (9) with a compound of the formula (10).

Carbostyril derivative represented by the formula (1) of the present invention can easily be converted into its acid-addition salt by reacting it with a pharmaceutically acceptable acid. The examples of such acid includes inorganic acids such as hydrochloric acid, sulfuric acid, phosphoric acid, hydrobromic acid and the like; organic acids such as oxalic acid, maleic acid, fumaric acid, malic acid, tartaric acid, citric acid, benzoic acid and the like. Among carbostyril derivatives represented by the formula (1) of the present invention, those having acidic group can easily be converted into their salts by reacting with basic compounds. The examples of such basic compounds includes sodium hydroxide, potassium hydroxide, calcium hydroxide, sodium carbonate, potassium hydrogen carbonate and the like. The desired compounds prepared by the procedures in the above-mentioned various reaction formulas can easily be isolated and purified by usual separation means such as solvent extraction, dilution, recrystallization, column chromatography, preparative thin layer chromatography and the like.

Carbostyril derivatives represented by the general formula (1) can be used in the form of usual pharmaceutical compositions which are prepared by using diluents or excipients such as fillers, bulking agents, binders, wetting agents, disintegrating agents, surface active agents, lubricants and the like. As to the pharmaceutical compositions, various types of administration unit forms can be selected depending on the therapeutical purposes, and the examples of pharmaceutical compositions are tablets, pills, powders, liquids, suspensions, emulsions, granules, capsules, suppositories, injection preparations (solutions and suspensions) and the like. For the purpose of shaping the pharmaceutical composition in the form of tablets, any excipients which are known and used widely in this field can also be used, for example carriers such as lactose, white sugar, sodium chloride, glucose, urea, starch, calcium carbonate, kaolin, crystalline cellulose, silicic acid and the like; binders such as water, ethanol, propanol, simple sirup, glucose solutions, starch solutions, gelatin solutions, carboxymethyl cellulose, shelac, methyl cellulose, potassium phosphate, polyvinylpyrrolidone and the like; disintegrating agents such as dried starch, sodium alginate, agar powder, laminalia powder, sodium hydrogen carbonate, calcium carbonate, fatty acid esters of polyoxyethylene sorbitan, sodium laurylsulfate, monoglyceride of stearic acid, starch, lactose and the like; disintegration inhibitors such as white sugar, stearin, coconut butter, hydrogenated oils; absorption accelerators such as quaternary ammonium base, sodium laurylsulfate and the like; wetting agents such as glycerin, starch and the like; adsorbing agents such as starch, lactose, kaolin, bentonite, colloidal silicic acid and the like; and lubricants such as purified talc, stearates, boric acid powder, polyethylene glycol and the like. If tablets are desired, they can be further coated with the usual coating materials to make the tablets as sugar coated tablets, gelatin film coated tablets, tablets coated with enteric coatings, tablets coated with films, double layered tablets and multi-layered tablets.

For the purpose of shaping the pharmaceutical composition in the form of pills, any excipients which are known and widely used in this field can also be used, for example, carriers such as lactose, starch, coconut butter, hardened vegetable oils, kaolin, talc and the like; binders such as gum arabi powder, tragacanth gum powder, gelatin, ethanol and the like; disintegrating agents such as agar, laminalia and the like.

For the purpose of shaping the pharmaceutical composition in the form of suppositories, any excipients which are known and widely used in this field can also be used, for example polyethylene glycols, coconut butter, higher alcohols, esters of higher alcohols, gelatin, semisynthesized glycerides and the like.

For the purpose of shaping the pharmaceutical composition in the form of injection preparations, solutions and suspensions are sterilized and are preferably made isotonic to blood. In making injection preparations, any carriers which are usually used in this field can also be used, for example, water, ethyl alcohol, propylene glycol, ethoxylated isostearyl alcohol, polyoxylated isostearyl alcohol, fatty acid esters of polyoxyethylene sorbitan. In these instances, adequate amounts of sodium chloride, glucose or glycerin can be added to the desired injection preparations to make them isotonic. Furthermore, usual dissolving agents, buffer agents, analgesic agents may be added. Yet further, if necessary, coloring agents, preservatives, perfumes, seasoning agents, sweetening agents agents and other medicines may also be added to the desired preparations during the treatment of schizophrenia.

The amount of carbostyril derivative of the general formula (1) or salt thereof to be contained in a pharmaceutical composition for treating schizophrenia according to the present invention is not specifically restricted and can suitably be selected from a wide range, usually it is contained 1 to 70%, preferably 1 to 30% by weight of the whole composition.

Administration methods of a pharmaceutical composition for treating schizophrenia of the present invention are not specifically restricted, and can be administered in various forms of preparations depending on the age of the patient, distinction of sex, other conditions, as well as conditions of the symptoms. For example, tablets, pills, solutions, suspensions, emulsions, granules and capsules are orally administered; and injection preparations are administered singly or mixed with injection transfusions such as glucose solutions and amino acid solutions intravenously; and if necessary, the injection preparations are administered singly intramuscularly, intracutaneously, subcutaneously or intraperitoneally. Suppositories are administered into the rectum.

The dosage of a pharmaceutical composition for treating schizophrenia according to the present invention are suitably selected according to the method of use, the age of the patient, distinction of sex, other conditions, as well as conditions of the symptoms, usually about 0.1 to 10 mg/kg of the body weight/day of carbostyril derivative of the general formula (1) as the active ingredient may be administered. Usually, 1 to 200 mg of the active ingredient may be contained in an administration unit form.

In the above-mentioned formula (1), the $C_1-C_3$ alkoxy group is a straight-chain or branched-chain alkoxy group having 1 to 3 carbon atoms, such as a methoxy group, an ethoxy group, a propoxy group, an isopropoxy group and the like, and among these, methoxy group and ethoxy group are preferable, and ethoxy group is the most preferable. Furthermore, the carbon-carbon bond between 3- and 4-positions in the carbostyril skeleton is preferably a single bond.

The present invention will be explained in detail by showing Reference Examples, Examples, Pharmacological test results and Examples of Pharmaceutical Compositions, however, the present invention are not restricted only thereto.

Reference Example 1

To a mixture of 6.08 g of 2-chloro-3-methylaniline, 9 g of di(2-bromoethyl)amine hydrobromide and 4 ml of water was added a solution of 0.8 g of potassium hydorxide and 2.5 ml of water 3 times of 1 hour interval at 100° C., then the reaction mixture was stirred at the same temperature for 9 hours. To the resultant reaction mixture was added potassium hydroxide to make the mixture alkaline, and the mixture was extracted with diethyl ether, washed with water, dried with anhydrous magnesium sulfate. The solvent was removed by evaporation and the residue thus obtained was purified by means of a silica gel column chromatography (eluent: 5%-methanol/chloroform), and obtained 3.41 g of 4-(2-chloro-3-methylphenyl)piperazine.

Light purple oily substance $^1$H-NMR (CDCl$_3$)δ: 2.38 (3H, s), 3.04 (8H, m), 6.93 (2H, m), 7.12 (1H, dd, J=7.7Hz, 7.7Hz)

Reference Examples 2-5

By procedures similar to those employed in the above mentioned Reference Example 1, by using suitable starting materials, there were prepared compounds of Reference Examples 2-5 as shown in the following Table 1.

TABLE 1

R—N⌒NH (piperazine ring with R—N and NH)

| Reference Example No. | R | $^1$H-NMR (CDCl$_3$) δ: |
|---|---|---|
| 2 | 3-methyl-2-nitrophenyl ($O_2N$, $CH_3$ substituted phenyl) | 2.45 (3H, s), 2.90 (4H, m), 3.05 (4H, m), 7.23 (1H, dd, J=8.0Hz, 2.0Hz), 7.28 (1H, dd, J=7.4Hz, 8.0Hz), 7.52 (1H, dd, J=7.4Hz, 2.0Hz) |
| 3 | 2-bromo-3-methylphenyl ($H_3C$, $Br$ substituted phenyl) | 2.42 (3H, s), 3.03 (8H, m), 6.90 (1H, d, J=7.9Hz), 6.95 (1H, d, J=7.5Hz), 7.17 (1H, dd, J=7.5Hz, 7.9Hz) |
| 4 | 2,3,5-trichlorophenyl (Cl, Cl, Cl substituted phenyl) | 3.05 (8H, m), 6.91 (1H, d, J=2.3Hz), 7.17 (1H, d, J=2.3Hz) |
| 5 | 2,3-dibromophenyl (Br, Br substituted phenyl) | 3.02 (8H, m), 6.98 (1H, dd, J=8.0Hz, 1.5Hz), 7.14 (1H, t, J=8.0Hz), 7.35 (1H, dd, J=8.0Hz, 1.5Hz) |

Reference Example 6

To a solution of 4.06 g of potassium carbonate with 400 ml of water was added 40 g of 7-hydroxy-3,4-dihydrocarbostyril and 158 g of 1,4-dibromobutane, then the mixture was refluxed for 3 hours. The reaction mixture thus obtained was extracted with dichloromethane, dried with anhydrous magnesium sulfate, then the solvent was removed by evaporation. The residue thus obtained was purified by means of a silica gel column chromatography (eluent: dichloromethane), and recrystallized from n-hexane-ethanol to yield 50 g of 7-(4-bromobutoxy)-3,4-dihydrocarbostyril.

Colorless needle crystals

Melting point: 110.5°–111.0° C.

Example 1

A suspension of 47 g of 7-(4-bromobutoxy)-3,4-dihydrocarbostyril, 35 g of sodium iodide with 600 ml of acetonitrile was refluxed for 30 minutes. To this suspension was added 40 g of 1-(2,3-dichlorophenyl)piperazine and 33 ml of triethylamine and the whole mixture was further refluxed for 3 hours. After the solvent was removed by evaporation, the residue thus obtained was dissolved in chloroform, washed with water then dried with anhydrous magnesium sulfate. The solvent was removed by evaporation, and the residue thus obtained was recrystallized from ethanol twice, to yield 57.1 g of 7-{4-[-4-(2,3-dichlorophenyl)-1-piperazinyl]butoxy}-3,4-dihydrocarbostyril.

Colorless flake crystals
Melting point: 139.0°–139.5° C.

One gram of 7-{4-[4-(2,3-dichlorophenyl)-1-piperazinyl]butoxy}-3,4-dihydrocarboxtyril was dissolved in 20 ml of ethanol by heating, then under stirring condition, an ethanol solution saturated with hydrogen chloride was added thereto, the crystals precipitated were collected by filtration and recrystallized from thanol to yield 0.75 g of 7-{4-[4-(2,3-dichlorophenyl)-1-piperazinyl]butoxy}-3,4-dihydrocarbostyril hydrochloride.

White powdery substance
Melting point: 214°–222° C. (decomposed).

One gram of 7-[4-.4-(2,3-dichlorophenyl)-1-piperazinyl]butoxy}-3,4-dihydrocarbostyril was dissolved in 10 ml of ethanol, then to this solution was added 4 ml of sulfuric acid-ethanol (1 ml of concentrated sulfuric acid/10 ml of ethanol), then the solvent was removed by evaporation. To the residue thus obtained was added 10 ml of ethanol and 30 ml of water, the mixture was heated to make it as a solution, recrystallized, and the crystals were collected by filtration, further recrystallized from ethanol-water to yield 1.02 g of 7-{4-[4-(2,3-dichlorophenyl)-1-piperazinyl]butoxy}-3,4-dihydrocarboxtyril·sulfate.

White powdery substance
Melting point: 220°–225° C.

By using 1.0 g of 7-{4-[4-(2,3-dichlorophenyl)-1-piperazinyl]butoxy}-3,4-dihydrocarbostyril and 290 mg of fumaric acid, and treated by procedures similar to those employed in the case of preparation of the sulfate as mentioned above, and recrystallized from ethanol to yield 0.97 g of 7-{4-[4-(2,3-dichlorophenyl)-1-piperazinyl]butoxy}-3,4-dihydrocarbostyril·fumarate.

White powdery substance
Melting point: 196°–198° C.

By using 1.0 g of 7-{4-[4-(2,3-dichlorophenyl)-1-piperazinyl]butoxy}-3,4-dihydrocarboxtyril and 290 mg of maleic acid, and treated by procedures similar to those employed in the case of preparation of the sulfate as mentioned above, and recrystallized from ethanol to yield 0.98 g of 7-{4-[4-(2,3-dichlorophenyl)-1-piperazinyl[butoxy}-3,4-dihydrocarbostyril·maleate.

White powdery substance
Melting point: 172°–180° C.

EXAMPLES 2–14

By using suitable starting materials, and by procedures similar to those employed in Example 1, there were prepared compounds of Examples 2–14 as shown in Table 2 as follows. In Table 2, compounds of Examples 11–14 are in the form of hydrochlorides.

TABLE 2

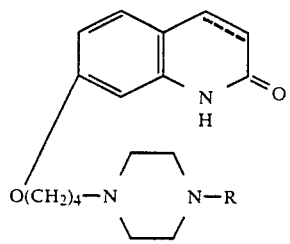

| Example No. | R | Carbon-carbon bond between 3- and 4- positions in carbostyril skeleton | Crystal form (Recrystallization solvent) | Melting point (°C.) |
|---|---|---|---|---|
| 2 | H₃C, NO₂ substituted phenyl | Single bond | Yellow needle crystals (Methanol) | 165–166 |
| 3 | Cl, CH₃ substituted phenyl | Single bond | Colorless flake crystals (Ethanol) | 133–134 |
| 4 | Br, CH₃ substituted phenyl | Single bond | Colorless needle crystals (Ethanol) | 125–126 |

TABLE 2-continued

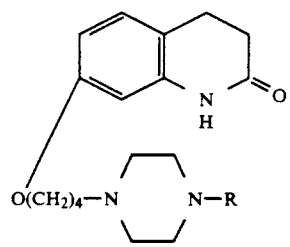

| Example No. | R | Carbon-carbon bond between 3- and 4- positions in carbostyril skeleton | Crystal form (Recrystallization solvent) | Melting point (°C.) |
|---|---|---|---|---|
| 5 | 3,5-di-Cl-phenyl | Single bond | White powdery substance (Ethanol) | 134–135 |
| 6 | 2-OC₂H₅-phenyl | Single bond | Colorless granular crystals (Ethanol) | 133–134 |
| 7 | 3,4,5-tri-Cl-phenyl | Single bond | White powdery substance (Methanol) | 174–176 |
| 8 | 2-OCH₃-phenyl | Single bond | White powdery substance (Methanol) | 125–126 |
| 9 | 2,3-di-Br-phenyl | Single bond | Pale brown flake crystals (Methanol) | 150–151 |
| 10 | 2,3-di-Cl-phenyl | Double bond | White powdery substance (Ethanol) | 144–146 |
| 11 | 2-OC₂H₅-phenyl | Double bond | White powdery substance (Ethanol) | 151 (decomp.) |

TABLE 2-continued

[Structure: 3,4-dihydrocarbostyril with 7-position substituent O(CH₂)₄-N(piperazine)-N-R]

| Example No. | R | Carbon-carbon bond between 3- and 4- positions in carbostyril skeleton | Crystal form (Recrystallization solvent) | Melting point (°C.) |
| --- | --- | --- | --- | --- |
| 12 | phenyl with OC₂H₅ | Single bond | Colorless fine needle crystals (Ethanol) | 214–218 |
| 13 | phenyl with O-n-C₃H₇ | Single bond | Pale brown powdery substance (Ethanol-diethyl ether) | 207–207.5 |
| 14 | phenyl with O-iso-C₃H₇ | Single bond | Pale brown powdery substance (Ethanol-diethyl ether) | 203–203.5 |

PHARMACOLOGICAL TESTS (a) Anti-apomorphine activity in mouse

Pharmacological test was conducted by using six mice in one test group. One hour after the oral administration of a test compound to a test mouse, apomorphine (1.25 mg/kg) was subcutaneously administered, and the stereotypy movements manifested were scored according to the method by Puech (Neuropharmacology, Vol. 20, pp. 1279, 1981). The anti-apomorphine activity performed by each of the test compounds were evaluated by the scored data as the indication thereof.

50% Effective dose ($ED_{50}$, mg/kg) of anti-apomorphine activity performed by a test compound is determined in that when the score obtained from the test group is lower than 50% of mean value of the score obtained from the control group, then it is defined as "positive" in anti-apomorphine activity.

(b) Anti-epinephrine lethal activity in mouse

By procedures similar to those described in Janssen, P., et al.: Arzneimittel Forschung, Vol. 13, pp. 205, (1963), the test was conducted by using six mice in one test group. One hour after the oral administration of a test compound to a test mouse, a lethal dose (1.5 mg/kg) of epinephrine was intravenously administered, and 4 hours after the intravenous administration, each of the mice in the test group was observed whether it is alive or not.

50% Effective dose ($ED_{50}$, mg/kg) of anti-epinephrine lethal activity performed by a test compound is determined from the amount thereof orally administered, and in the case that the mouse is alive is determined as "positive" in anti-epinephrine lethal activity.

The test results are shown in Table 3 as follows.

| Test compound No. | |
| --- | --- |
| 1 | Compound of Example 1 (Free form) |
| 2 | Compound of Example 2 |
| 3 | Compound of Example 3 |
| 4 | Compound of Example 4 |
| 5 | Compound of Example 5 |
| 6 | Compound of Example 12 |
| 7 | Compound of Example 7 |
| 8 | Compound of Example 8 |
| 9 | Compound of Example 9 |
| 10 | Compound of Example 10 |
| 11 | Compound of Example 11 |
| 12 | Compound of Example 13 |
| 13 | Compound of Example 14 |

TABLE 3

| Test compound No. | Anti-apomorphine activity ($ED_{50}$ mg/kg) (A) | Anti-epinephrine activity ($ED_{50}$ mg/kg) (B) | (B)/(A) |
| --- | --- | --- | --- |
| 1 | 0.18 | >128 | >711 |
| 2 | 0.3 | >128 | >426.7 |
| 3 | 0.4 | >64 | >160 |
| 4 | 0.4 | >64 | >160 |
| 5 | 0.5 | >128 | >256 |
| 6 | 0.1 | 3.7 | 37 |
| 7 | 0.4 | >128 | >320 |
| 8 | 0.2 | 2.5 | 12.5 |

TABLE 3-continued

| Test compound No. | Anti-apomorphine activity (ED$_{50}$ mg/kg) (A) | Anti-epinephrine activity (ED$_{50}$ mg/kg) (B) | (B)/(A) |
| --- | --- | --- | --- |
| 9 | 0.6 | >256 | >426.7 |
| 10 | 0.36 | >128 | >355 |
| 11 | 0.12 | 3.8 | 31.6 |
| 12 | 0.5 | 1.58 | 3.16 |
| 13 | 0.2 | 0.24 | 1.2 |

Example of Preparation of Pharmaceutical Composition -1

| | |
| --- | --- |
| 7-{4-[4-(2,3-dichlorophenyl)-1-piperazinyl]butoxy}-3,4-dihydrocarbostyril | 5 mg |
| Starch | 132 mg |
| Magnesium stearate | 18 mg |
| Lactose | 45 mg |
| Total | 200 mg |

By using usual procedures, tablets containing the above formulation per one tablet were prepared.

Example of Preparation of Pharmaceutical Composition-2

| | |
| --- | --- |
| 7-{4-[4-(2-ethoxyphenyl)-1-piperazinyl]-butoxy}-3,4-dihydrocarbostyril | 500 mg |
| Polyethylene glycol (Molecular weight: 4,000) | 0.3 g |
| Sodium chloride | 0.9 g |
| Polyoxyethylene sorbitan monooleate | 0.4 g |
| Sodium metabisulfite | 0.1 g |
| Methyl p-hydroxybenzoate | 0.18 g |
| Propyl p-hydroxybenzoate | 0.02 g |
| Distilled water for injection | 100 ml |

The above-mentioned methyl p-hydroxybenzoate, propyl p-hydroxybenzoate, sodium metabisulfite and sodium chloride were dissolved in distilled water for injection at 80° C. with stirring. The resulting solution was cooled to 40° C. then 7-{4-[4-(2-ethoxyphenyl)-1-piperazinyl]butoxy}-3,4-dihydrocarboxtyril, polyethylene glycol and polyoxyethylene sorbitan monooelate were dissolved in the above-mentioned solution in this order, then the predetermined volume of the injection solution was adjusted by adding the distilled water for injection, and was sterilized by filtration by using a suitable filter paper, then 1 ml each of the desired injection solution was filled in an ampul.

What is claimed is:

1. A carboxtyril compound or salt thereof of the formula,

[Structure: 3,4-dihydrocarbostyril with O(CH$_2$)$_4$—N(piperazinyl)N—R substituent]

wherein R is a group of the formula

[Structure: phenyl with R$^1$]

wherein R$^1$ is a C$_1$–C$_3$ alkoxy group; a group of the formula

[Structure: phenyl with R$^2$, R$^3$, R$^4$]

wherein R$^2$ and R$^3$ are at the same time, both chlorine atoms, or both bromine atoms and R$^4$ is a hydrogen atom or a chlorine atom; a 2-methyl-3-nitrophenyl group; a 3,5-dichlorophenyl group; or a group of the formula

[Structure: phenyl with R$^5$, R$^6$]

wherein R$^5$ is a chlorine atom or a bromine atom and R$^6$ is a methyl group; the carbon-carbon bond between the 3- and 4-positions in the carboxtyril skeleton being a single or a double bond.

2. The carboxtyril compound or salt thereof of claim 1, wherein R is a group of the formula

[Structure: phenyl with R$^1$]

3. The carboxtyril compound or salt thereof of claim 2, wherein R$^1$ is a methoxy group or an ethoxy group.

4. The carboxtyril compound or salt thereof of claim 1, wherein R is a group of the formula

[Structure: phenyl with R$^2$, R$^3$, R$^4$]

5. The carbostyril compound or salt thereof of claim 4, wherein R$^2$ and R$^3$ are chlorine atoms and R$^4$ is a hydrogen atom.

6. The carbostyril compound or salt thereof of claim 4, wherein R$^2$ and R$^3$ are bromine atoms and R$^4$ is a hydrogen atom.

7. The carbostyril compound or salt thereof of claim 4, wherein R$^2$, R$^3$ and R$^4$ are chlorine atoms.

8. The carbostyril compound or salt thereof of claim 1, wherein R is a 2-methyl-3-nitrophenyl group or a 3,5-dichlorophenyl group.

9. The carbostyril compound or salt thereof of claim 1, wherein R is a group of the formula

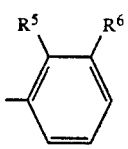

10. The carbostyril compound or salt thereof of claim 9, wherein $R^5$ is a chlorine atom.

11. The carbostyril compound or salt thereof of claim 9, wherein $R^5$ is a bromine atom.

12. 7-{4-[4-(2,3-Dichlorophenyl)-1-piperazinyl]butoxy}-3,4-dihydrocarbostyril.

13. 7-{4-[4-(b 2,3-Dichlorophenyl)-1-piperazinyl]butoxy}carbostyril.

14. 7-{4-[4-(2-Ethoxyphenyl)-1-piperazinyl]butoxy}-3,4-dihydrocarbostyril.

15. 7-{4-[4-(2-Ethoxyphenyl)-1-piperazinyl]butoxy}carbostyril.

16. A pharmaceutical composition for treating schizophrenia containing, as the active ingredient, a carbostyril compound or pharmaceutically acceptable salt thereof of claim 1 and a pharmaceutically acceptable carrier.

17. The pharmaceutical composition of claim 16, wherein the carbostyril compound or salt thereof is 7-{4-[4-(2,3-dichlorophenyl)-1-piperazinyl]butoxy}-3,4-dihydrocarbostyril.

18. The pharmaceutical composition of claim 16, wherein the carbostyril compound or salt thereof is 7-{4-[4-(2,3-dichlorophenyl)-1-piperazinyl]butoxy}carbostyril.

19. The pharmaceutical composition of claim 16, wherein the carbostyril compound or salt thereof is 7-{4-[4-(2-ethoxyphenyl)-1-piperazinyl]butoxy}-3,4-dihydrocarbostyril.

20. The pharmaceutical composition of claim 16, wherein the carbostyril compound or salt thereof is 7-{4-[4-(2-ethoxyphenyl)-1-piperazinyl]butoxy}carbostyril.

21. The pharmaceutical composition for treating schizophrenia containing, as the active ingredient, a carbostyril compound or pharmaceutically acceptable salt thereof of claim 3 and a pharmaceutically acceptable carrier.

* * * * *

UNITED STATES PATENT AND TRADEMARK OFFICE

(12)   CERTIFICATE EXTENDING PATENT TERM
       UNDER 35 U.S.C. § 156

| | | | |
|---|---|---|---|
| (68) | PATENT NO. | : | 5,006,528 |
| (45) | ISSUED | : | April 9, 1991 |
| (75) | INVENTOR | : | Yasuo Oshiro, et al. |
| (73) | PATENT OWNER | : | Otsuka Pharmaceutical Co., Ltd. |
| (95) | PRODUCT | : | ABILIFY® (aripiprazole) |

This is to certify that an application under 35 U.S.C. § 156 has been filed in the United States Patent and Trademark Office, requesting extension of the term of U.S. Patent No. 5,006,528 based upon the regulatory review of the product ABILIFY® (aripiprazole) by the Food and Drug Administration. Since it appears that the requirements of the law have been met, this certificate extends the term of the patent for the period of

(94)                Five years from October 20, 2009, the original expiration date of the patent, subject to the payment of maintenance fees as provided by law, with all rights pertaining thereto as provided by 35 U.S.C. § 156(b).

I have caused the seal of the United States Patent and Trademark Office to be affixed this 12th day of October 2005.

Jon W. Dudas
Under Secretary of Commerce for Intellectual Property and
Director of the United States Patent and Trademark Office

UNITED STATES PATENT AND TRADEMARK OFFICE
CERTIFICATE OF CORRECTION

PATENT NO. : 5,006,528

DATED : April 9, 1991

INVENTOR(S) : Yasuo Oshiro et al.

It is certified that error appears in the above-identified patent and that said Letters Patent is hereby corrected as shown below:

Claim 1, column 17, line 54, change "carboxtyril" to --carbostyril--;

column 18, line 35, change "carboxtyril" to --carbostyril--.

Claim 2, column 18, line 37, change "carboxtyril" to --carbostyril--.

Claim 3, column 18, line 47, change "carboxtyril" to --carbostyril--.

Claim 4, column 18, line 49, change "carboxtyril to --carbostyril--.

Claim 13, column 19, line 20, change "(b 2,3-Dichlorophenyl)" to --2,3-Dichlorophenyl)--.

UNITED STATES PATENT AND TRADEMARK OFFICE
CERTIFICATE OF CORRECTION

PATENT NO. : 5,006,528

DATED : April 9, 1991

INVENTOR(S) : Yasuo Oshiro et al

It is certified that error appears in the above-identified patent and that said Letters Patent is hereby corrected as shown below:

Abstract, line 1, after "thereof" insert --useful for breaking schizophrenia--.

Signed and Sealed this

Twenty-seventh Day of April, 1993

*Attest:*

MICHAEL K. KIRK

*Attesting Officer*     *Acting Commissioner of Patents and Trademarks*

UNITED STATES PATENT AND TRADEMARK OFFICE

(12)      CERTIFICATE EXTENDING PATENT TERM
UNDER 35 U.S.C. § 156

| | | | |
|---|---|---|---|
| (68) | PATENT NO. | : | 5,006,528 |
| (45) | ISSUED | : | April 9, 1991 |
| (75) | INVENTOR | : | Yasuo Oshiro, et al. |
| (73) | PATENT OWNER | : | Otsuka Pharmaceutical Co., Ltd. |
| (95) | PRODUCT | : | ABILIFY® (aripiprazole) |

This is to certify that an application under 35 U.S.C. § 156 has been filed in the United States Patent and Trademark Office, requesting extension of the term of U.S. Patent No. 5,006,528 based upon the regulatory review of the product ABILIFY® (aripiprazole) by the Food and Drug Administration. Since it appears that the requirements of the law have been met, this certificate extends the term of the patent for the period of

(94)                      Five years from October 20, 2009, the original expiration date of the patent, subject to the payment of maintenance fees as provided by law, with all rights pertaining thereto as provided by 35 U.S.C. § 156(b).

I have caused the seal of the United States Patent and Trademark Office to be affixed this <u>12th day</u> of <u>October 2005</u>.

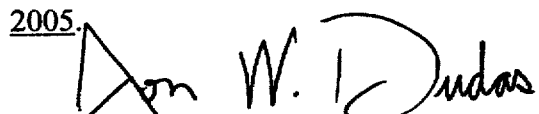

Jon W. Dudas
Under Secretary of Commerce for Intellectual Property and Director of the United States Patent and Trademark Office

UNITED STATES PATENT AND TRADEMARK OFFICE
CERTIFICATE OF CORRECTION

PATENT NO. : 5,006,528
APPLICATION NO. : 07/424719
DATED : June 6, 2006
INVENTOR(S) : Yasuo Oshiro et al.

Page 1 of 1

It is certified that error appears in the above-identified patent and that said Letters Patent is hereby corrected as shown below:

In the Abstract, please replace formula (1) with the following:

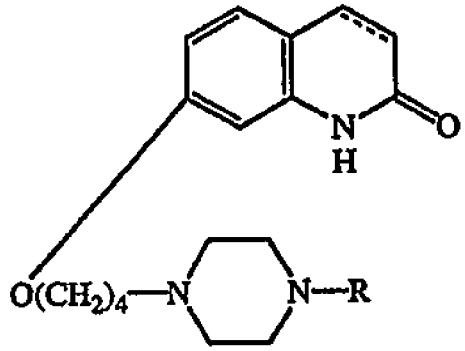

Signed and Sealed this

Thirty-first Day of July, 2007

JON W. DUDAS
*Director of the United States Patent and Trademark Office*

UNITED STATES PATENT AND TRADEMARK OFFICE
CERTIFICATE OF CORRECTION

PATENT NO.       : 5,006,528 C1
APPLICATION NO.  : 90/007167
DATED            : June 13, 2006
INVENTOR(S)      : Yasuo Oshiro et al.

It is certified that error appears in the above-identified patent and that said Letters Patent is hereby corrected as shown below:

In the Abstract, please replace formula (1) with the following:

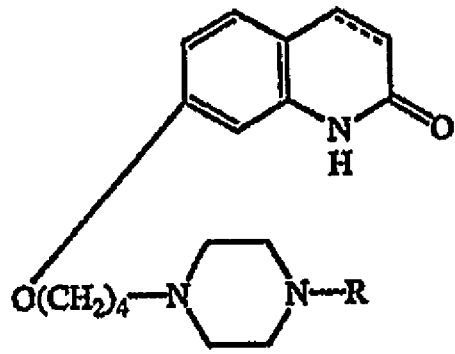

This certificate supersedes Certificate of Correction issued July 31, 2007.

Signed and Sealed this

Twenty-first Day of August, 2007

JON W. DUDAS
*Director of the United States Patent and Trademark Office*

(12) EX PARTE REEXAMINATION CERTIFICATE (5396th)
United States Patent
Oshiro et al.

(10) Number: US 5,006,528 C1
(45) Certificate Issued: Jun. 13, 2006

(54) CARBOSTYRIL DERIVATIVES

(75) Inventors: Yasuo Oshiro, Tokushima (JP); Seiji Sato, Itano (JP); Nobuyuki Kurahashi, Tokushima (JP)

(73) Assignee: Otsuka Pharmaceutical Co., Ltd., Rockville, MD (US)

Reexamination Request:
No. 90/007,167, Aug. 11, 2004

Reexamination Certificate for:
Patent No.: 5,006,528
Issued: Apr. 9, 1991
Appl. No.: 07/424,719
Filed: Oct. 20, 1989

Certificate of Correction issued Apr. 27, 1993.

(30) Foreign Application Priority Data

Oct. 31, 1988 (JP) .............................. 63-276953

(51) Int. Cl.
*A61K 31/497* (2006.01)
*A61K 31/00* (2006.01)
*C07D 401/12* (2006.01)

(52) U.S. Cl. ....................... 514/253; 544/363
(58) Field of Classification Search ................ None
See application file for complete search history.

(56) References Cited

U.S. PATENT DOCUMENTS

| | | | |
|---|---|---|---|
| 3,362,956 A | 1/1968 | Archer |
| 3,983,121 A | 9/1976 | Murthi et al. |
| 3,994,900 A | 11/1976 | Krapcho et al. |
| 4,147,869 A | 4/1979 | Nakagawa et al. |
| 4,210,753 A | 7/1980 | Tominaga et al. |
| 4,234,584 A | 11/1980 | Lattrell et al. |
| 4,234,585 A | 11/1980 | Winter et al. |
| 4,289,883 A | 9/1981 | Tominaga et al. |
| 4,734,416 A | 3/1988 | Banno et al. |
| 4,746,661 A | 5/1988 | Lattrell et al. |
| 4,803,203 A | 2/1989 | Caprathe et al. |
| 4,824,840 A | 4/1989 | Banno et al. |
| 4,914,094 A | 4/1990 | Oshiro et al. |

FOREIGN PATENT DOCUMENTS

| | | |
|---|---|---|
| AU | A-50252/85 | 5/1986 |
| CA | 1117110 | 1/1982 |
| DE | 29 12 105 C2 | 10/1979 |
| DE | 29 53 723 C2 | 10/1979 |
| EP | 0 005 828 | 12/1979 |
| EP | 0 006 506 | 1/1980 |
| EP | 0 182 247 | 5/1986 |
| EP | 0 226 441 A2 | 6/1987 |
| FR | 2 344 538 | 10/1977 |
| GB | 1 212 174 | 11/1970 |
| GB | 2017701 B | 10/1978 |
| GB | 2071094 A | 9/1981 |
| JP | 54-130587 | 10/1979 |
| JP | 55-124766 | 9/1980 |
| JP | 55-127371 | 10/1980 |
| JP | 56-46812 | 4/1981 |
| JP | 56-49359 | 5/1981 |
| JP | 56-49360 | 5/1981 |
| JP | 56-49361 | 5/1981 |
| JP | 56-049357 A | 5/1981 |
| JP | 56-049362 A | 5/1981 |
| JP | 57-145872 | 9/1982 |
| JP | 58-43952 | 3/1983 |
| JP | 58-203968 A | 11/1983 |
| JP | 62-149664 | 7/1987 |

OTHER PUBLICATIONS

Two Abstract for JP–56–049362 A.

(Continued)

*Primary Examiner*—Rita Desai

(57) ABSTRACT

A novel carbostyril derivative and salt thereof useful for breaking schizophrenia represented by the formula (1)

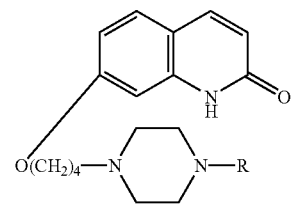

(1)

(wherein R is a group of the formula

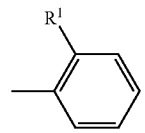

((wherein $R^1$ is a $C_1$–$C_3$ alkoxy group)), a group of the formula

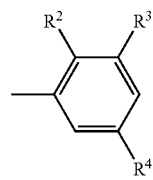

((wherein $R^2$ and $R^3$ are each, at the same time, a chlorine atom, a bromine atom; and $R^4$ is a hydrogen atom or a chlorine atom)), 2-methyl-3-nitrophenyl group, 3,5-dichlorophenyl group, or a group of the formula

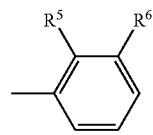

((wherein $R^5$ is a chlorine atom or a bromine atom; and $R^6$ is a methyl group)); the carbon-carbon bond between 3- and 4-position in the carbostyril skeleton is a single or double bond).

OTHER PUBLICATIONS

Two Abstract for JP–56–049357 A.
Abstract for JP–58–203968 A.
Banno et al., "Studies of 2(1H)–Quinolinone Derivatives as Neuroleptic Agents, I, Synthesis and Biological Activities of (4–Phenyl–1–piperazinyl)–propoxy–2(1H)–quinolinone Derivatives," Chem. Pharm. Bull., vol. 36, No. 11, pp. 4377–4388 (Nov. 25, 1988).
*Molecular Design for Creative Synthesis of Pharmaceuticals* (*Souyaku No Tameno Bunshisekkei*), Chemistry—An Extra Issue, 191–200 (Sep. 1989) (with partial English translation).
Abstract of DE 29 12 105 C2.
Abstract of DE 29 53 723 C2.
Abstract of JP 54–130587.
Abstract of JP 55–124766.
Abstract of JP 55–127371.
Abstract of JP 56–46812.
Abstract of JP 56–49359.
Abstract of JP 56–49360.
Abstract of JP 56–49361.
Abstract of JP 57–145872.
Abstract of JP 58–43952.
Abstract of JP 62–149664.
Kiuchi et al., "Effect of 7–[3–(4–(2,3–Dimethylphenyl) Piperazinyl)Propoxy]–2(1H)–Quinolinone (OPC–4392), A Newly Synthesized Agonist For Presynaptic Dopamine $D_2$ Receptor, On Tyrosine Hydroxylation In Rat Striatal Slices," Life Sciences, vol. 42, No. 3, pp. 343–349 (1988) (National Diet Library in Japan accepted this document on Feb. 12, 1988).

Yasuda et al., "7–[3–(4–(2,3–Dimethylphenyl)Piperazinyl) Propoxy]–2(1H)–Quinolinone (OPC–4392), A Presynaptic Dopamine Autoreceptor Agonist And Postsynaptic D2 Receptor Antagonist," Life Sciences, vol. 42, No. 20, pp. 1941–1954 (1988) (National Diet Library in Japan accepted this document on May 19, 1988).

Sasa et al., "Presynaptic Inhibition of Excitatory Input From the Substantia Nigra to Caudate Nucleus Neurons by a Substituted Quinolinone Derivative 7–[3–(4–(2,3–Dimethylphenyl)Piperazinyl)Propoxy]–2(1H)–Quinolinone (OPC–4392)," Life Sciences, vol. 43, No. 3, pp. 263–269 (Jul. 18, 1988).

Gerbaldo et al., "The Effect of OPC–4392, a Partial Dopamine Receptor Agonist on Negative Symptoms: Results of an Open Study," Pharmacopsychiatry, vol. 21, pp. 387–388 (Nov. 1988).

Murasaki et al., "Phase 1 Study of a New Antipsychotic Drug, OPC–4392," Prog. Neuro–Psychopharmacol & Biol Psychiat., vol. 12, No. 5, pp. 793–802 (1988) (Library of Osaka University accepted this document on Sep. 20, 1988).

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 2, lines 3–10:

Among carbostyril derivatives known in prior art, those disclosed in U.S. Pat. No. 4,734,416; Canadian Patent No. 1,117,110; British Patent No. 2,017,701; German Patent Nos. [2,911,108, 1,912,105] *2,912,105* and 2,953,723; Japanese Patent Kokai (Laid-open) Patent Nos. 54-130,587 (1979), 55-127,371, (1980) and 62-149,664 (1987) are having chemical structural formula of upper conception of carbostyril derivatives of the present invention.

AS A RESULT OF REEXAMINATION, IT HAS BEEN DETERMINED THAT:

The patentability of claims 1–21 is confirmed.

New claims 22–24 are added and determined to be patentable.

*22. A method of treating schizophrenia in a patient comprising administering a pharmaceutical composition to said patient containing, as an active ingredient, a carbostyril compound or salt thereof of claim 1.*

*23. The method of treating schizophrenia of claim 22, wherein the carbostyril compound or salt thereof is 7-(4-[4-(2,3-dichlorophenyl)-1-piperazinyl]butoxy)-3,4-dihydrocarbostyril or a salt thereof.*

*24. The method of treating schizophrenia of claim 22, wherein the carbostyril compound or salt thereof is 7-[4-[4-(2,3-dichlorophenyl)-1-piperazinyl]butoxy]-carbostyril or a salt thereof.*

* * * * *